US00PP30916P2

(12) United States Plant Patent
Smutzer

(10) Patent No.: US PP30,916 P2
(45) Date of Patent: Oct. 1, 2019

(54) ***CAMELLIA* PLANT NAMED 'GNC CAM1'**

(50) Latin Name: *Camellia sasanqua*
Varietal Denomination: GNC CAM1

(71) Applicant: Harry Joe Smutzer, Park Hill, OK (US)

(72) Inventor: Harry Joe Smutzer, Park Hill, OK (US)

(73) Assignee: Greenleaf Nursery Company, Park Hill, OK (US)

( * ) Notice: Subject to any disclaimer, the term of this patent is extended or adjusted under 35 U.S.C. 154(b) by 0 days.

(21) Appl. No.: 15/998,363

(22) Filed: Aug. 7, 2018

(51) Int. Cl.
*A01H 5/02* (2018.01)

(52) U.S. Cl.
USPC ..... Plt./243

(58) Field of Classification Search
USPC ..... Plt./243
See application file for complete search history.

*Primary Examiner* — Annette H Para
(74) *Attorney, Agent, or Firm* — C. A. Whealy

(57) ABSTRACT

A new and distinct cultivar of *Camellia* plant named 'GNC CAM1', characterized by its uniform, compact, outwardly branching and low-mounding plant habit; moderately vigorous growth habit; freely branching habit, dense and bushy appearance; low requirement for frequent pruning to maintain uniform plant habit; yellow green and darker yellow green variegated leaves that are lightly blushed with greyed orange when developing in the spring; red purple-colored semi-double type flowers; and good garden performance.

3 Drawing Sheets

Botanical designation: *Camellia sasanqua.*
Cultivar denomination: 'GNC CAM1'.

BACKGROUND OF THE INVENTION

The present Invention relates to a new and distinct cultivar of *Camellia* plant, botanically known as *Camellia sasanqua*, commercially known as Royal Flush Shishi and hereinafter referred to by the name 'GNC CAM1'.

The new *Camellia* plant is a naturally-occurring whole plant mutation of *Camellia sasanqua* 'Shishi Gashira', not patented. The new *Camellia* plant was discovered and selected by the Inventor as a single plant from within a population of plants of 'Shishi Gashira' in an outdoor nursery in El Campo, Tex. in 2010.

Asexual reproduction of the new *Camellia* plant by semi-hardwood cuttings in a controlled environment in El Campo, Tex. since July, 2011 shown that the unique features of this new *Camellia* plant are stable and reproduced true to type in successive generations.

SUMMARY OF THE INVENTION

Plants of the new *Camellia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'GNC CAM1'. These characteristics in combination distinguish 'GNC CAM1' as a new and distinct cultivar of *Camellia:*

1. Uniform, compact, outwardly branching and low-mounding plant habit.
2. Moderately vigorous growth habit.

3. Freely branching habit, dense and bushy appearance; low requirement for frequent pruning to maintain uniform plant habit.
4. Yellow green and darker yellow green variegated leaves that are lightly blushed with greyed orange when developing in the spring.
5. Red purple-colored semi-double type flowers.
6. Good garden performance, tolerant to full sunlight to shade conditions.

Plants of the new *Camellia* differ from plants of the patent, 'Shishi Gashira', primarily in the following characteristics:

1. Plants of the new *Camellia* are compact, uniform and low-mounding in plant habit whereas plants of 'Shishi Gashira' are open and loose requiring frequent pruning to develop and maintain a uniform plant habit.
2. Leaves of plants of the new *Camellia* are variegated whereas leaves of plants of 'Shishi Gashira' are dark green in color without any variegation.
3. Flowers of plants of the new *Camellia* are red purple in color whereas flowers of plants of 'Shishi Gashira' are light red purple (pink) in color.

Plants of the new *Camellia* can be compared to the plants of *Camellia sasanqua* 'Mine No Yuki', not patented. In side-by-side comparisons plants of the new *Camellia* differ from plants of the 'Mine No Yuki' in the following characteristics:

1. Plants of the new *Camellia* are uniform, compact, outwardly branching and low-mounding in plant habit whereas plants of 'Mine No Yuki' are upright, open and loose requiring frequent pruning to develop and maintain a uniform plant habit.
2. Plants of the new *Camellia* are more freely-branching than plants of 'Mine No Yuki'.
3. Leaves of plants of the new *Camellia* are variegated whereas leaves of plants of 'Mine No Yuki' are dark green in color without any variegation.

4. Flowers of plants of the new *Camellia* are semi-double type and red purple in color whereas flowers of plants of 'Mine No Yuki' are double type and white in color.

BRIEF DESCRIPTION OF THE PHOTOGRAPHS

The accompanying colored photographs illustrate the overall appearance of the new *Camellia* plant showing the colors as true as it is reasonably possible to obtain in colored reproductions of this type. Colors in the photographs may differ slightly from the color values cited in the detailed botanical description, which accurately describe the colors of the new *Camellia* plant.

The photograph on the first sheet is a side perspective view of a typical plant of 'GNC CAM1' grown in an outdoor nursery.

The photograph on the second sheet is a close-up view of a typical plant of 'GNC CAM1' grown during the spring showing developing and fully developed leaves.

The photograph on the third sheet is a close-up view of a typical open flower of 'GNC CAM1'.

DETAILED BOTANICAL DESCRIPTION

The aforementioned photographs and following observations and measurements describe plants grown in El Campo and Fort Worth, Tex. in 7-gallon containers in an outdoor nursery during the winter, spring and early summer and under cultural practices typical of commercial *Camellia* production. During the production of the plants, day temperatures ranged from −3° C. to 38° C. and night temperatures ranged from −5° C. to 26° C. Plants were five years old when the photographs and description were taken. In the following description, color references are made to The Royal Horticultural Society Colour Chart, 2007 Edition, except where general terms of ordinary dictionary significance are used.

Botanical classification: *Camellia sasanqua* 'GNC CAM1'.

Parentage: Naturally-occurring whole plant mutation of *Camellia sasanqua* 'Shishi Gashira', not patented.

Propagation:

*Type*.—Semi-hardwood cuttings.

*Time to initiate roots, summer*.—About 45 to 55 days at temperatures about 27° C. to 30° C.

*Time to initiate roots, winter*.—About 65 to 75 days at temperatures about 16° C. to 17° C.

*Time to produce a rooted young plant, summer*.—About 100 to 120 days at temperatures about 27° C. to 30° C.

*Time to produce a rooted young plant, winter*.—About 120 to 140 days at temperatures about 16° C. to 17° C.

*Root description*.—Medium in thickness, fibrous; typically white maturing to brown in color, actual color of the roots is dependent on substrate composition, water quality, fertilizer type and formulation, substrate temperature and physiological age of roots.

*Rooting habit*.—Freely branching; medium density to dense.

Plant description:

*Plant form and growth habit*.—Perennial evergreen shrub; uniform, compact, outwardly branching and low-mounding plant habit; moderately vigorous growth habit; moderate growth rate.

*Branching habit*.—Freely branching habit; lateral branches potentially developing at every node; dense and bushy appearance; low requirement for pruning to maintain uniform plant habit.

*Plant height*.—About 27.5 cm.

*Plant diameter, area of spread*.—About 51 cm.

*Lateral branch description*.—Length, secondary branches: About 21 cm. Diameter, secondary branches: About 5 mm. Internode length: About 8 mm. Strength: Strong. Aspect: About 45° from vertical. Texture and luster: Pubescent; slightly glossy; woody with development. Color, young stems: Close to 166B becoming closer to 166A with development. Color, older stems: Close to 199A to 199B.

*Leaf description*.—Arrangement: Alternate, single. Length: About 5.5 cm. Width: About 2.6 cm. Shape: Elliptic. Apex: Acuminate. Base: Cuneate. Margin: Serrate. Venation pattern: Pinnate. Texture and luster, upper and lower surfaces: Smooth, glabrous; leathery; glossy. Color: Developing leaves, upper surface: During the spring, close to N144A to N144B with random irregular central sectors, close to between 144A and 146A and blushed with close to 163B to 163C; during the summer, close to 146A with random irregular central sectors, close to 147A. Developing leaves, lower surface: During the spring, close to N144B; during the summer, close to 146B. Fully expanded leaves, upper surface: Darker green than 147A; midvein, close to 146A and lateral venation, darker green than 147A; color is maintained during the autumn and winter. Fully expanded leaves, lower surface: Darker green than 146A; midvein, close to 146B and lateral venation, darker green than 146A; color is maintained during the autumn and winter.

*Petioles*.—Length: About 5 mm. Diameter: About 2 mm. Texture and luster, upper and lower surfaces: Pubescent; leathery; slightly glossy. Color, upper surface: Close to 146A. Color, lower surface: Close to 146A to 146B.

Flower description:

*Flower arrangement and appearance*.—Semi-double type rotate flowers, flowers terminal and axillary; freely flowering habit with usually about 35 flowers and flower buds developing per plant; flowers face mostly outwardly.

*Natural flowering season*.—Plants of the new *Camellia* flower during the winter and early spring in Texas.

*Postproduction longevity*.—Plants maintain good flower substance for about three to four days on the plant; flowers persistent.

*Fragrance*.—None detected.

*Flower diameter*.—About 4.1 cm.

*Flower depth*.—About 2 cm.

*Flower buds*.—Length: About 7.5 mm. Diameter: About 4.5 mm. Shape: Ovoid. Texture and luster: Smooth, glabrous; matte. Color: Close to between 144A and 146A.

*Petals and petaloids*.—Quantity and arrangement: About 23 imbricate petals and petaloids arranged in numerous whorls. Length: About 1.75 cm to 2.1 cm. Width: About 1.3 cm to 1.5 cm. Shape: Obovate. Apex: Obcordate to rounded. Base: Cuneate. Margin: Entire; undulate. Texture and luster, upper and lower surfaces: Smooth, glabrous; velvety; matte. Color: When opening and fully opened, upper surface: Close to 58B; venation, close to 58B; color does not change with development. When opening and fully opened, lower surface: Close to 58B to 58C; venation, close to 58B to 58C; color does not change with development.

*Sepals*.—Quantity and arrangement: About five imbricate sepals arranged in an ovate-shaped calyx. Length: About 5.5 mm. Width: About 4 mm. Shape: Ovate. Apex: Cuspidate. Base: Truncate. Margin: Entire. Texture and luster, upper and lower surfaces: Smooth, glabrous; leathery; matte. Color, upper and lower surfaces: Close to between 144A and 146A.

*Peduncles*.—Length: About 4 mm. Diameter: About 2 mm. Aspect: About 30° to 45° from stem axis. Strength: Strong. Texture and luster: Smooth, glabrous; matte. Color: Close to 146A to 146B.

*Reproductive organs*.—Androecium: Quantity per flower: About 47. Filament length: About 6 mm. Filament color: Proximally, close to 52D; distally, close to NN155A. Anther shape: Oblong. Anther size: About 1.6 mm. Anther color: Close to 14A to 14B. Pollen amount: Scarce. Pollen color: Close to 14A. Gynoecium: Quantity of pistils per flower: About five. Pistil length: About 5 mm. Style length: About 4 mm. Style color: Close to 2D. Stigma diameter: Less than 1 mm. Stigma color: Close to 2D. Ovary color: Close to 10A to 10B.

*Fruits and seeds*.—Fruit and seed production have not been observed on plants of the new *Camellia* to date.

Garden performance: Plants of the new *Camellia* have been observed have good garden performance and to tolerate rain, wind, full sunlight, shade and are suitable for USDA Hardiness Zones 7 to 9.

Pathogen & pest resistance: Plants of the new *Camellia* have not been observed to be resistant to pathogens and pests common to *Camellia* plants to date.

It is claimed:

1. A new and distinct cultivar of *Camellia* plant named 'GNC CAM1' as illustrated and described.

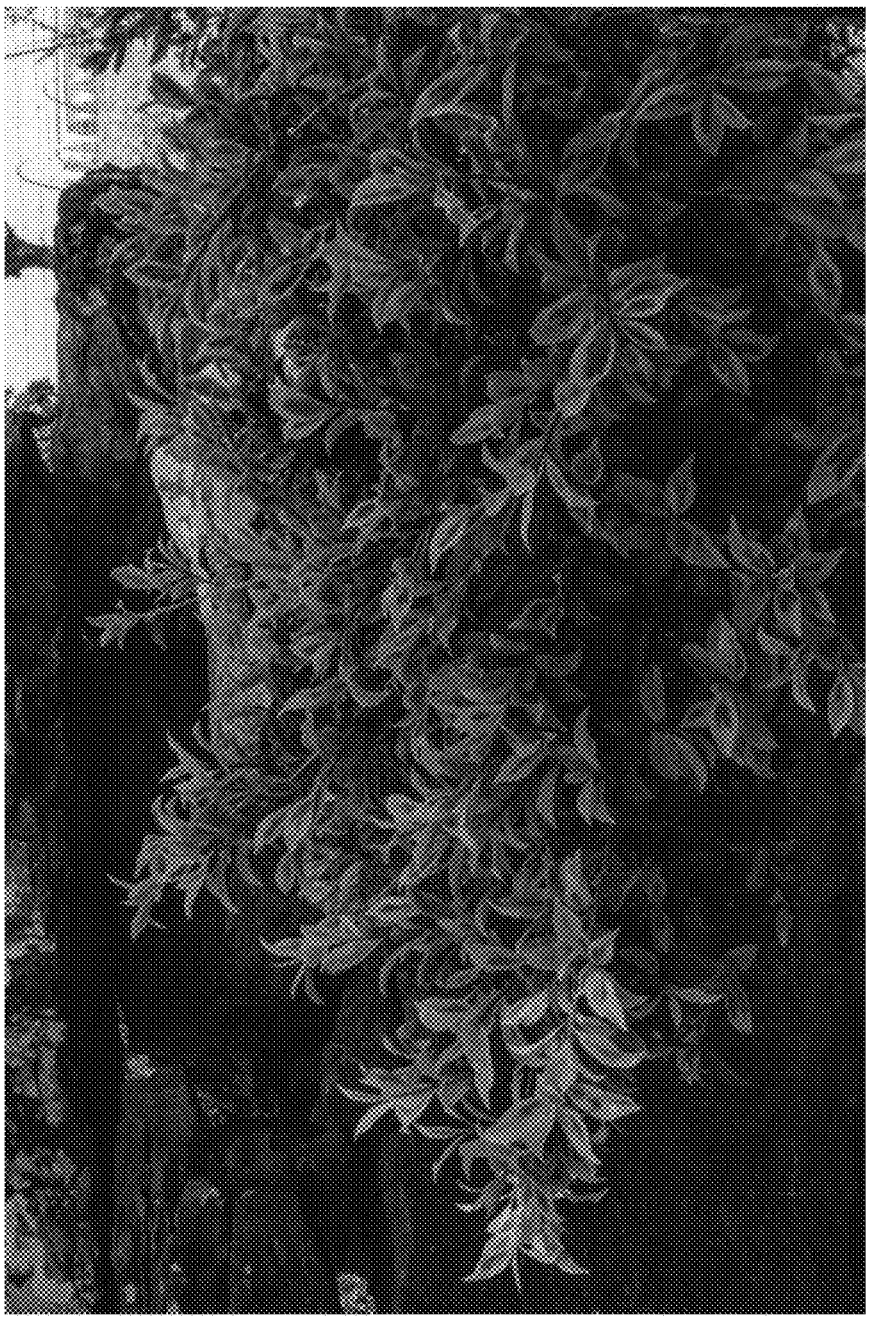

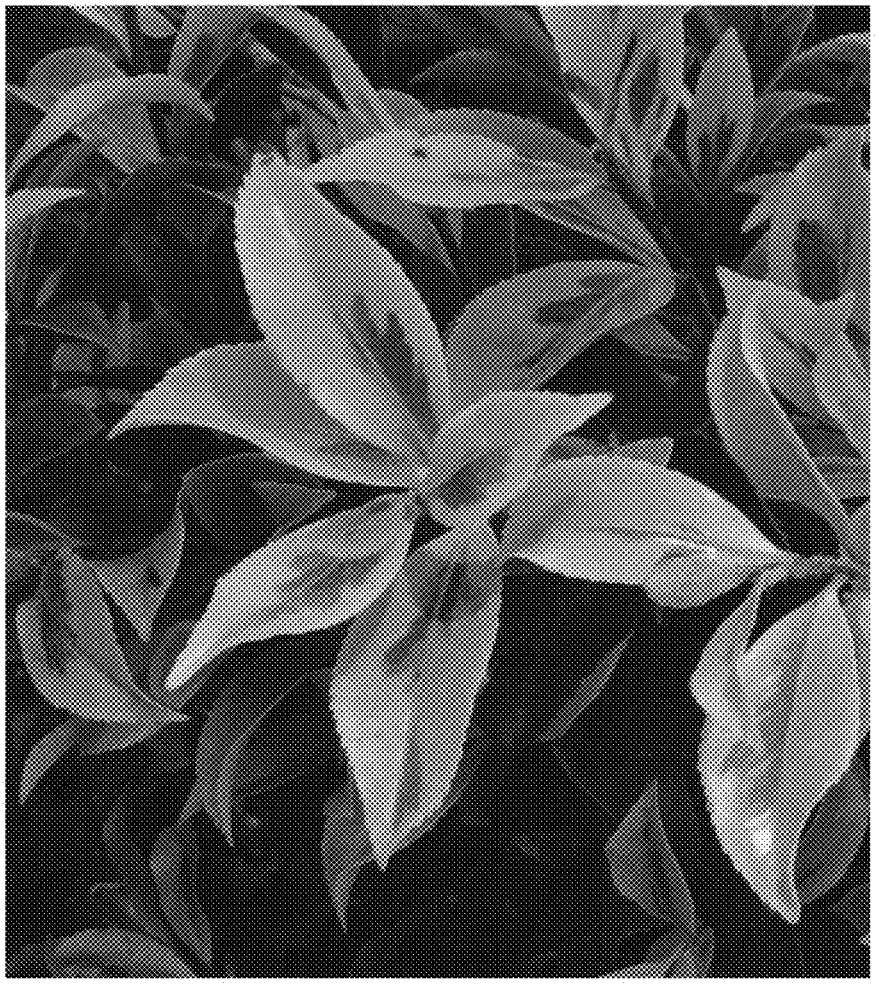

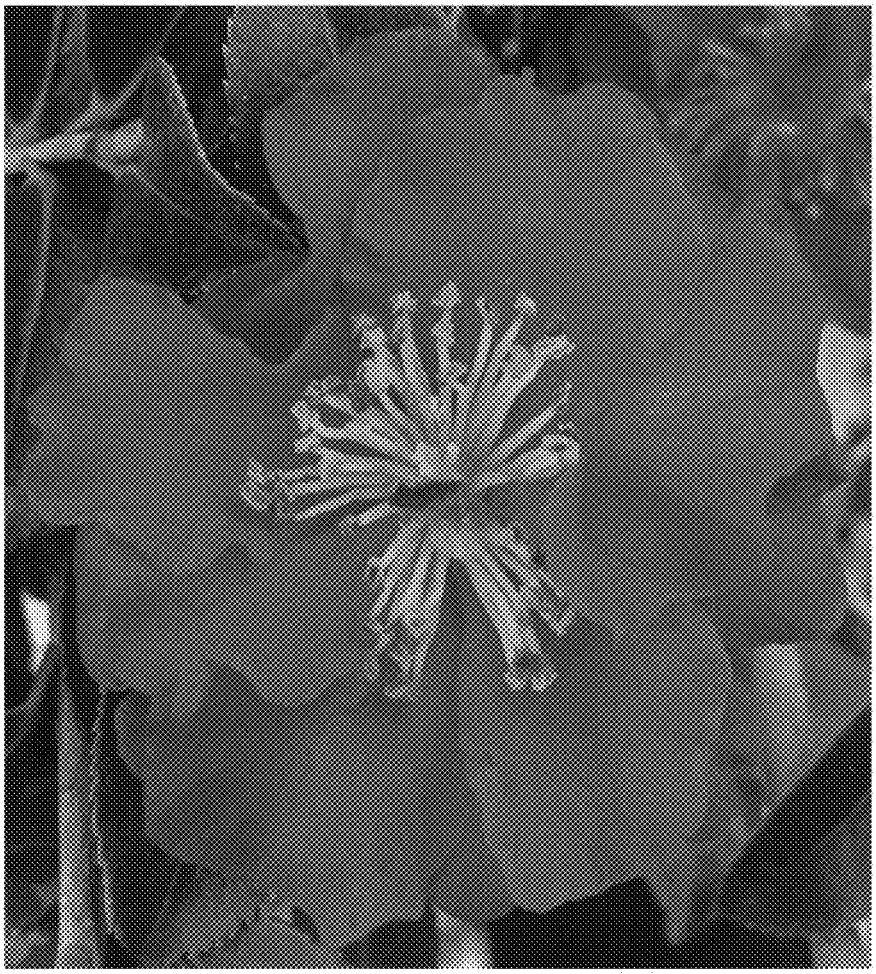

* * * * *